(12) United States Patent
Brahms et al.

(10) Patent No.: US 7,943,354 B2
(45) Date of Patent: May 17, 2011

(54) METHOD TO REMOVE BISULFITE BY-PRODUCTS FROM ENZYME COMPOSITIONS

(75) Inventors: John Brahms, Morris Plains, NJ (US); James G. Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 576 days.

(21) Appl. No.: 11/961,661

(22) Filed: Dec. 20, 2007

(65) Prior Publication Data

US 2008/0138748 A1 Jun. 12, 2008

Related U.S. Application Data

(62) Division of application No. 11/205,568, filed on Aug. 17, 2005, now Pat. No. 7,332,315.

(51) Int. Cl.
*C12N 9/00* (2006.01)
(52) U.S. Cl. .................................. 435/183; 435/188
(58) Field of Classification Search .................. None
See application file for complete search history.

(56) References Cited

U.S. PATENT DOCUMENTS

| | | |
|---|---|---|
| 3,634,081 A | 1/1972 | Forst et al. |
| 3,909,408 A | 9/1975 | Ishida et al. |
| 4,196,175 A | 4/1980 | Jensen |
| 4,264,760 A | 4/1981 | Meyer |
| 4,370,239 A | 1/1983 | Jensen |
| 5,071,664 A | 12/1991 | Brown |
| 5,488,141 A | 1/1996 | Bauer, Jr. et al. |
| 6,051,687 A | 4/2000 | Meeker |
| 6,875,809 B2 | 4/2005 | Rozynov et al. |
| 2003/0232884 A1 | 12/2003 | Fink |
| 2004/0161591 A1 | 8/2004 | Rozynov et al. |

OTHER PUBLICATIONS

Fox C.H. et al. Formaldehyde fixation, a review article, The Journal of Histochemistry and Cytochemistry, 1985, 33(8): 845-853.*
Abe E. et al. Preventive effects of amino acids and glutathione on the formaldehyde-induced denaturation of myofibrillar proteins, Fisheries Science, Jun. 2003, 69(3): 605-614.*
Anderson P. J. Purification and quantitation of glutaraldehyde and its effect on several enzyme activities in skeletal muscle, The J. Histochem. Cytochem., 1967, 15(11): 652-661.*
Bliss et al. "Action of Formaldehyde on Enzymes and on Certain Proteids". 1899. Downloaded from www.jem.org on Dec. 4, 2006, pp. 47-80.
Zhang Yinquan, "Discovery History for Cyclic Structure of Monosaccharide" Dept. of Chem., School of Biological and Chem. Engineering, Guangzhou Uni., vol. 21,pp. 69-72; Feb. 2006.

* cited by examiner

*Primary Examiner* — Jon P Weber
*Assistant Examiner* — Satyendra K Singh
(74) *Attorney, Agent, or Firm* — Nikhil A. Heble

(57) ABSTRACT

Provided are methods of removing bisulfite material from a composition that contains a bisulfite material and an enzyme. The method includes contacting the composition with a compound containing at least one aldehyde functional group to form an aldehyde-bisulfite complex, whereby the aldehyde-bisulfite complex may be separated from the composition.

11 Claims, No Drawings

METHOD TO REMOVE BISULFITE BY-PRODUCTS FROM ENZYME COMPOSITIONS

CROSS REFERENCE TO RELATED APPLICATIONS

This application is a divisional application of U.S. application Ser. No. 11/205,568, filed 17 Aug. 2005, which is now a U.S. Pat. No. 7,332,315 (issued on Feb. 19, 2008 to same inventive entity), and which is incorporated herein by reference.

BACKGROUND OF THE INVENTION

Various types of enzymes may be included in oral formulations to act as therapeutic agents. For example, enzymes may be included to hydrolyze oral polysaccharides or to inhibit bacterial growth. More specifically, for example, it was reported that enzymes such as mutanase, dextranase, papain, and 1,3-glucanase can be employed in oral formulations for removing plaque deposits.

Generally, enzymes by nature are vulnerable to changes of environment such as pH, temperature, and ion concentration, and thus it is usually necessary to take measures to protect enzymes to maintain intended oral-care efficacy of the enzymes. To improve performance of enzymes, enzyme-stabilizing agents, such as chelating agents and anti-oxidizing agents, have been suggested. Examples of such enzyme-stabilizing agents are EDTA, sodium gluconate, sodium bisulfite, metal gallates, sodium stannate, and ascorbic acid.

Among the enzyme-stabilizing agents, however, bisulfite materials, i.e., compounds containing bisulfite ion, are shown to be toxic to some individuals, and/or often alter the organoleptic properties of an oral care formulation. Therefore, it may be desirable to remove or reduce bisulfite materials in enzyme compositions before the compositions are further processed and delivered to consumers. Even though bisulfite materials can be removed through conventional techniques such as base extraction and neutralization by an oxidizing agent, these techniques often adversely affect the catalytic activity of enzymes in oral compositions. Thus, it is desirable to introduce an alternative method for removing bisulfite materials which does not negatively affect activity of enzymes in a composition to be treated. To date, there has been no convenient method to remove bisulfite materials from enzyme compositions, which method can be conducted under neutral, non-oxidizing conditions.

BRIEF SUMMARY OF THE INVENTION

In accordance with the present invention, there is provided a method of removing bisulfite materials from a composition comprising bisulfite materials and one or more enzymes. The method comprises contacting the composition with a compound containing at least one aldehyde functional group to form an aldehyde-bisulfite complex; whereby the aldehyde-bisulfite complex may be separated from the composition.

In one embodiment, the method comprises contacting the composition with a compound containing at least one aldehyde functional group such as aldose sugar to form an aldehyde-bisulfite complex and separating the aldehyde-bisulfite complex from the composition, wherein the enzyme is selected from the group consisting of papain, bromelain, a serine protease, chymotrypsin ficin, glucose oxidase, galactose oxidase lactose peroxidase, lactoferrin, lysozyme, lipolytic enzymes, alcalase, a carbohydrase, a glucoamylasae, a dextranase, a mutase, a tannase, and a lipase.

In another embodiment, there is provided a method of removing bisulfite materials from a composition containing bisulfite materials and an enzyme, wherein the method comprises contacting the composition with a matrix having at least one aldehyde functional group to form an aldehyde-bisulfite complex and separating the matrix bound bisulfite from the composition.

In yet another embodiment, there is further provided an enzyme composition substantially devoid of bisulfite materials. The enzyme composition is obtainable by a method of contacting the composition with a compound containing at least one aldehyde functional group to form an aldehyde-bisulfite complex and then separating the aldehyde-bisulfite complex from the composition.

DETAILED DESCRIPTION OF THE INVENTION

The present invention relates to a method of removing a bisulfite material from a composition containing one or more enzymes. More particularly, the invention relates to a method of removing bisulfite ion by contacting the enzyme composition with a compound containing at least one aldehyde functional group to form an aldehyde-bisulfite complex and separating the bisulfite complex from the composition. Also, the present invention relates to a bisulfite-free enzyme composition which is prepared by contacting the enzyme composition with a compound containing at least one aldehyde functional group to form an aldehyde-bisulfite complex and separating the bisulfite complex from the composition.

The present invention provides a method of removing bisulfite materials from an enzyme composition by employing a compound having at least one aldehyde functional group that forms a complex with the bisulfite material and separating the aldehyde-bisulfite complex from the composition. Preferably, the process is carried out under substantially neutral, non-oxidizing conditions, thereby obtaining a substantially bisulfite-free composition containing enzymes that are not substantially degradation.

The term "degradation" used herein denotes decrease of enzyme activity relative to an enzyme composition from which bisulfite material has not been extracted. In accordance with the present invention, preferably, more than 50% of the enzyme activity, more than 80% or more than 90% is retained after the step of contacting bisulfite with aldehyde, and thereafter the step of separating the bisulfite-aldehyde complex, or after both steps.

The term "bisulfite materials" means compounds containing bisulfite ion chemically bound or as a component of a chemical complex, such as sodium bisulfite or other bisulfite salts.

To remove bisulfite from an enzyme composition, the present invention employs a compound containing at least one aldehyde functional group. An "aldehyde" is defined as one species of carbonyl compound having the structure R-CHO, wherein the R group can be either aromatic or aliphatic group. To obtain a substantially bisulfite-free composition containing enzymes not substantially degraded, it may be desirable to select an aldehyde that is capable of forming a complex with bisulfite material under neutral, non-oxidizing condition. An aldehyde of the present invention may be a monofunctional aldehyde having low molecular weight, e.g., less than about 1000 Daltons. The aldehyde may be an aldose sugar.

A substantially bisulfite-free composition is obtained by separating the bisulfite-aldehyde complex from the composition. Such separation may be accomplished by any separation technique known in the art such as a chemical or a physical method, or a combination of chemical and physical methods. Examples of separation techniques adaptable to the present invention include, but are not limited to, filtering, differential diffusion, column separation, and bead separation, and separation by localization or sequestration.

Additionally, the separation may be accomplished by subjecting the composition to an object or article to which the aldehyde is attached, forming the complex, and removing the object or article to with the now aldehyde-bisulfite complex is attached. Alternatively, in order to obtain a composition with substantially undegraded enzymes, it may be desirable to maintain a substantially neutral, non-oxidizing condition throughout the steps of contacting bisulfite material and enzyme composition and thereafter separating the bisulfite-aldehyde complex. For example, pH of the enzyme solution may be kept within a range of about 5 to about 8, and ionic strength is maintained.

A method of removing bisulfite in accordance with the present invention can be applicable to a composition containing any type of enzyme. Advantageously, the present invention may be utilized to treat an enzyme composition which is eventually for purpose of contacting skin or mucous membrane of human or animal. For example, the enzyme composition may be any one that can be incorporated into an oral care or personal care product. Examples of such enzymes include, but are not limited to, carbohydrases such as glucoamylase, enzymes extracted from natural fruit products such as proteases, carbohydrases such as alpha-amylase, beta-amylase and tannase, and lipases such as plant lipase, gastric lipase and pancreatic lipase. Preferably, an enzyme in a composition to be treated by the present invention may be derived from a botanical source. Enzymes useful in the practice of the present invention may be selected from the group consisting of alpha and beta-amylase, dextranase, mutanase, the naturally occurring enzymes such as papain (from papaya), and bromelain (from pineapple), serine proteases such as chymotrypsin, ficin, alcalase, lysozyme, pectinase, and glucanase.

In accordance with an embodiment of the present invention, there is provided a method employing a matrix containing at least one aldehyde functional group to make removal of a bisulfite-aldehyde complex convenient. The method using a matrix containing at least one aldehyde functional group may be operable under the same conditions as those for a method of removing bisulfite without using a matrix. A matrix with an aldehyde functional group may be a conventional one, for example, selected from the group consisting of porous and non-porous beads, films, specks, and particles. In another embodiment, a matrix containing at least one aldehyde functional group may be dispersed on a support to help in separating a bisulfite-aldehyde complex. Any type of support known in the art may be used for the invention. Examples of support includes, but not limited to, column, container, filter, sponge, and gel.

In yet another embodiment, there is provided an enzyme composition substantially devoid of bisulfite material which is prepared by a method of removing bisulfite material in accordance with the present invention, wherein the enzyme composition is produced by contacting the composition with a compound containing at least one aldehyde functional group to form an aldehyde-bisulfite complex and separating the aldehyde-bisulfite complex from the composition. Since an enzyme composition of the present invention is prepared under neutral, non-oxidizing condition, activity of the enzymes in the composition is not substantially degraded. Preferably, about 90% of the activity of the enzyme remains undegraded. The enzyme composition produced by the method of the present invention is substantially free of bisulfite material, and accordingly, may be advantageously used in an oral care or personal care products, such as dentifrices, skin care products, and hair and nail care products.

The invention is further illustrated but not limited by the following Examples. Variations of the following examples are possible without departing from the scope of the invention.

Although the invention has been described with reference to specific examples, it will be apparent to one skilled in the art that various modifications may be made thereto which fall within its scope.

We claim:

1. A method of removing bisulfite material from a composition comprising bisulfite material and at least one enzyme, the method comprising the steps of contacting the composition with a matrix having at least one monofunctional aldehyde having low molecular weight to form an aldehyde-bisulfite complex and separating the aldehyde-bisulfite complex formed from the composition, wherein the monofunctional aldehyde is an aldose sugar.

2. The method of claim 1, wherein the separation step is selected from a group consisting of filtering, differential diffusion, column separation, and bead separation.

3. The method of claim 1 wherein the monofunctional aldehyde is combined with the composition at a pH range of about 5 to about 8.

4. The method of claim 1, wherein the at least one enzyme is not substantially degraded after the formation of the aldehyde-bisulfate complex.

5. The method of claim 4, wherein about 90% of an activity of the enzyme remains undegraded.

6. The method of claim 1, wherein the at least one enzyme is not substantially degraded after the step of separating the aldelyde-bisulfite complex.

7. The method of claim 6, wherein about 90% of an activity of the enzyme remains undegraded.

8. The method of claim 1, wherein the method further comprises separating a matrix bound aldehyde-bisulfite complex formed by the contacting step from the composition.

9. The method of claim 1, wherein the matrix is selected from a group consisting of porous and non-porous beads, films, specks, and particles.

10. The method of claim 1, wherein the matrix is dispersed on a support.

11. The method of claim 10, wherein the support is selected from the group consisting of column, container, filter, sponge, and gel.

* * * * *